United States Patent
Elsberg

(10) Patent No.: US 6,287,287 B1
(45) Date of Patent: Sep. 11, 2001

(54) DISPOSABLE ABSORBENT ARTICLES HAVING PASSIVE SIDE BONDS AND ADJUSTABLE FASTENING SYSTEMS

(75) Inventor: Laura Linda Elsberg, Appleton, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 0 days.

(21) Appl. No.: 09/100,574

(22) Filed: Jun. 19, 1998

(51) Int. Cl.[7] .............................. A61F 13/15; A61F 13/20
(52) U.S. Cl. ................... 604/385.03; 604/386; 604/387; 604/391
(58) Field of Search .............................. 604/358, 385.1, 604/385.2, 391, 392, 389, 385.03

(56) References Cited

U.S. PATENT DOCUMENTS

| | | | |
|---|---|---|---|
| 4,409,049 | * 10/1983 | Passafiume et al. | 156/164 |
| 4,973,326 | * 11/1990 | Wood et al. | 604/391 |
| 5,300,057 | * 4/1994 | Miller et al. | 604/390 |
| 5,368,585 | * 11/1994 | Dokken | 604/393 |
| 5,374,262 | * 12/1994 | Keuhn, Jr. et al. | 604/391 |
| 5,386,595 | * 2/1995 | Kuen et al. | 2/400 |
| 5,531,732 | * 7/1996 | Wood | 604/391 |
| 5,795,433 | 8/1998 | Niedermeyer . | |
| 5,904,802 | 5/1999 | Niedermeyer . | |
| 5,919,334 | 7/1999 | Niedermeyer . | |
| 6,022,430 | 2/2000 | Blenke et al. . | |
| 6,022,431 | 2/2000 | Blenke et al. . | |
| 6,022,432 | 2/2000 | Elsberg et al. . | |
| 6,036,805 | 3/2000 | McNichols . | |

FOREIGN PATENT DOCUMENTS

| | | |
|---|---|---|
| 0597331 B1 | 11/1997 | (EP) . |
| 2 308 290 A | 6/1997 | (GB) . |
| 9-287 U | 5/1997 | (JP) . |
| WO 97/47265 A1 | 12/1997 | (WO) . |

* cited by examiner

Primary Examiner—John G. Weiss
Assistant Examiner—Michele Kidwell
(74) Attorney, Agent, or Firm—Jeffrey B. Curtin; Alyssa A. Dudkowski

(57) ABSTRACT

A prefastened disposable absorbent article includes a pair of primary fasteners which are located on the opposed side edges in one the waist regions of the article. The primary fasteners overlap and releasably engage the opposite waist region of the absorbent article to provide the prefastened absorbent article. The prefastened disposable absorbent article further includes a pair of passive side bonds which are located inward of the primary fasteners on the one waist region. The passive side bonds releasably connect the overlapped portion of the one waist region to the opposite waist region to assist in maintaining the prefastened absorbent article in a prefastened condition. The side bonds also prevent shifting of the waist regions of the article relative to each other during use. The article may also include at least one secondary fastener which is located in one of the waist regions of the absorbent article. The secondary fastener is configured to releasably engage the opposite waist region of the absorbent article to conform the waist regions of the article to a wearer's body after the article has been pulled on over the hips of the wearer.

48 Claims, 4 Drawing Sheets

DISPOSABLE ABSORBENT ARTICLES HAVING PASSIVE SIDE BONDS AND ADJUSTABLE FASTENING SYSTEMS

FIELD OF THE INVENTION

The present invention relates to disposable absorbent articles which are adapted to contain body exudates. More particularly, the present invention relates to prefastened disposable absorbent articles which have passive side bonds and adjustable fastening systems to maintain the articles about the waist of the wearer.

BACKGROUND OF THE INVENTION

It is desired that absorbent articles such as diapers, training pants or incontinence garments provide a close, comfortable fit about the wearer and contain body exudates. Moreover, it is desirable that such absorbent articles, after being soiled, can be removed from the wearer in a convenient and dean manner without undesirably soiling the care giver or surrounding area such as the clothes of the wearer. In certain circumstances, it is also desirable that such absorbent articles are capable of being pulled up or down over the hips of the wearer to allow the wearer or caregiver to easily pull the article on and easily remove the article if it has not been soiled. For example, such absorbent articles can assist in the toilet training of children.

Conventional diapers are not provided in a prefastened condition and have typically included a front waist portion and a back waist portion which are releasably connected about the hips of the wearer during use by conventional fasteners such as adhesive tape fasteners or hook and loop type fasteners. For example, the conventional fasteners have typically included a pair of fasteners, such as adhesive tape tabs, located on the outermost comers of the diaper in the back waist region of the diaper and a complimentary fastener, such as a taping panel, located on the outer surface of the outer cover of the diaper in the front waist portion of the diaper. In such a configuration, the diaper has been positioned between the legs of the wearer and the adhesive tape tabs have been releasably attached to the taping panel to secure the back waist portion to the front waist portion of the diaper to secure the diaper about the waist of the wearer. Such conventional diapers are easy to fasten about and remove from the wearer after use without undesirably soiling the care giver. However, such conventional diapers are not prefastened before use and thus are not configured to be pulled up or down over the hips of the wearer when the fasteners are attached.

Several attempts have been made to provide absorbent articles which effectively contain body exudates and are capable of being pulled up or down over the hips of the wearer. For example, some conventional absorbent articles, such as conventional training pants, have included integral side panels which connect the front waist portion to the back waist portion of the absorbent article. The side panels have been made stretchable such that the waist opening of the absorbent article can expand to allow the absorbent article to be pulled up or down over the hips of the wearer if desired. Such side panels have also been designed such that they may be tom to remove the training pant from the wearer after it has been soiled.

However, many of such attempts have not been completely satisfactory. For example, absorbent articles such as training pants have not always been able to achieve a close conforming fit to the wearer while still being able to expand enough to be pulled up and down over the hips of the wearer. Often such training pants fit the waist of the wearer loosely which can undesirably result in leaks. As a result, many of such training pant articles have not contained bodily exudates as effectively as conventional diaper-type articles which can be adjusted to achieve a more conforming fit to the wearer. Moreover, the removal of soiled absorbent articles which have integral side panels, such as conventional training pants, has not always been completely satisfactory. For example, the side panels have been difficult to tear when attempting to remove the article from the waist of the wearer instead of pulling the article down over the hips of the wearer.

Accordingly, despite the attempts to develop improved absorbent articles, there remains a need for absorbent articles which can provide the benefits of conventional training pants and conventional diapers. That is, there remains a need for absorbent articles which conform to the wearer to effectively contain bodily exudates, which are capable of being pulled up and down over the hips and buttocks of the wearer, and which are readily secured about and removed from the wearer in a convenient and clean manner. Moreover, there is a need for disposable absorbent articles which include waist sections which are releasably prefastened such that the article can be reliably pulled on over the wearers legs and hips.

SUMMARY OF THE INVENTION

In response to the difficulties and problems discussed above, a new prefastened disposable absorbent article which has passive side bonds and an adjustable fastening system has been discovered. In one aspect, the present invention concerns a prefastened disposable absorbent article which defines an absorbent, a front waist region, a back waist region, a crotch region which extends between and connects the waist regions and a pair of opposed side edges. The prefastened absorbent article includes a pair of primary fasteners which are located on the opposed side edges in one of the waist regions. The primary fasteners overlap and releasably engage the opposite waist region of the absorbent article to provide the prefastened absorbent article. The article further includes a pair of passive side bonds which are located inward of the primary fasteners. The passive side bonds releasably connect an overlapped portion of the one waist region to the opposite waist region to assist in maintaining the prefastened absorbent article in a prefastened condition.

In another aspect, the present invention concerns a prefastened disposable absorbent article which defines an absorbent, a front waist region, a back waist region, a crotch region which extends between and connects the waist regions and a pair of opposed ear regions on one of the waist regions which overlap the opposite waist region. The absorbent article includes a pair of primary fasteners which are located on the opposed ear regions and which are releasably engaged to the opposite waist region of the absorbent article to provide the prefastened absorbent article. The article further includes a belt segment which defines opposed end portions and which is located in the one waist region and a pair of secondary fasteners which are located on the opposed end portions of the belt segment. The secondary fasteners are configured to releasably engage the opposite waist region to conform the waist regions to a wearers body after the prefastened absorbent article is pulled on over a wearer's hips. The article also includes a pair of passive side bonds which are located inward of the primary fasteners on the opposed ear regions. The passive bonds releasably connect an overlapped portion of the ear regions to the opposite waist region to assist in maintaining the prefastened absorbent article in a prefastened condition.

In still another aspect, the present invention concerns a prefastened disposable absorbent article which defines a front waist region, a back waist region, a crotch region which extends between and connects the waist regions and a pair of opposed side edges. The absorbent article includes an outer cover and an absorbent chassis. The absorbent chassis includes a backsheet which is connected to the outer cover, a bodyside liner which is connected to the backsheet in a superposed relation and an absorbent core disposed between the backsheet and the bodyside liner. The absorbent article includes a pair of primary fasteners which are located on the outer cover on the laterally opposed side edges of the back waist region of the absorbent article. The primary fasteners are configured to releasably engage an outer surface of the absorbent article in the front waist region of the absorbent article. The article further includes a belt segment which is located in the back waist region of the absorbent article and which defines a pair of opposed end portions and a pair of secondary fasteners which are located on the opposed end portions of the belt segment. The secondary fasteners are configured to releasably engage the outer surface of the front waist region to further conform the waist regions to a wearer's body after the prefastened absorbent article is pulled on over a wearer's hips. The article also includes a pair of passive side bonds which are located inward of the primary fasteners on the back waist region. The passive side bonds releasably connect an overlapped portion of the back waist region to the front waist region to assist in maintaining the prefastened absorbent article in a prefastened condition.

In yet another aspect, the present invention concerns a prefastened disposable absorbent article which defines an absorbent, a front waist region, a back waist region, a crotch region which extends between and connects the waist regions and a pair of opposed side edges. The absorbent article includes a pair of primary fasteners which are located on the opposed side edges in one of the waist regions. The primary fasteners are releasably engaged to the opposite waist region of the disposable absorbent article thereby defining a waist perimeter dimension. The absorbent article also includes a waist size adjustment means for reducing the waist perimeter dimension of the absorbent article without releasing the primary fasteners to conform the waist regions to a wearer's body after the prefastened absorbent article has been pulled on. The article also includes a pair of passive side bonds which are located inward of the primary fasteners on the one waist region and which releasably connect an overlapped portion of the one waist region to the opposite waist region to assist in maintaining the prefastened absorbent article in a prefastened condition.

The present invention advantageously provides a prefastened disposable absorbent article which includes the combination of passive side bonds and an adjustable fastening system for improved fit and performance. The absorbent article of the present invention is capable of being reliably pulled up or down over the hips of the wearer to assist in the toilet training of the wearer similar to conventional training pants. Moreover, similar to conventional diapers, the absorbent article of the present invention can advantageously be applied to and removed from the wearer after it has been soiled with relative ease and cleanliness.

BRIEF DESCRIPTION OF THE DRAWINGS

The present invention will be more fully understood and further advantages will become apparent when reference is made to the following detailed description of the invention and the accompanying drawings wherein like numerals represent like elements. The drawings are merely representative and are not intended to limit the scope of the appended claims.

DETAILED DESCRIPTION OF THE INVENTION

The present invention concerns prefastened disposable absorbent articles which are configured to closely conform to the body of the wearer to effectively contain body exudates while being capable of being pulled up or down over the hips and buttocks of the wearer. The prefastened disposable absorbent articles can also be easily secured to and removed directly from the waist of the wearer. As such, the absorbent articles of the present invention can function similar to conventional training pants in their prefastened configuration or they can be unfastened prior to or during use to function similar to conventional diapers.

The prefastened disposable absorbent articles are adapted to be worn adjacent to the body of a wearer to absorb and contain various exudates discharged from the body. As used herein, the term "disposable" refers to articles which are intended to be discarded after a limited use and which are not intended to be laundered or otherwise restored for reuse. The prefastened disposable absorbent articles of the present invention will be described in terms of a prefastened disposable diaper article which is adapted to be worn by infants about the lower torso. It is understood that the disposable absorbent articles of the present invention are equally adaptable for use as other types of absorbent articles such as adult incontinent products, training pants, feminine hygiene products, other personal care or health care garments, and the like.

Figure 1:
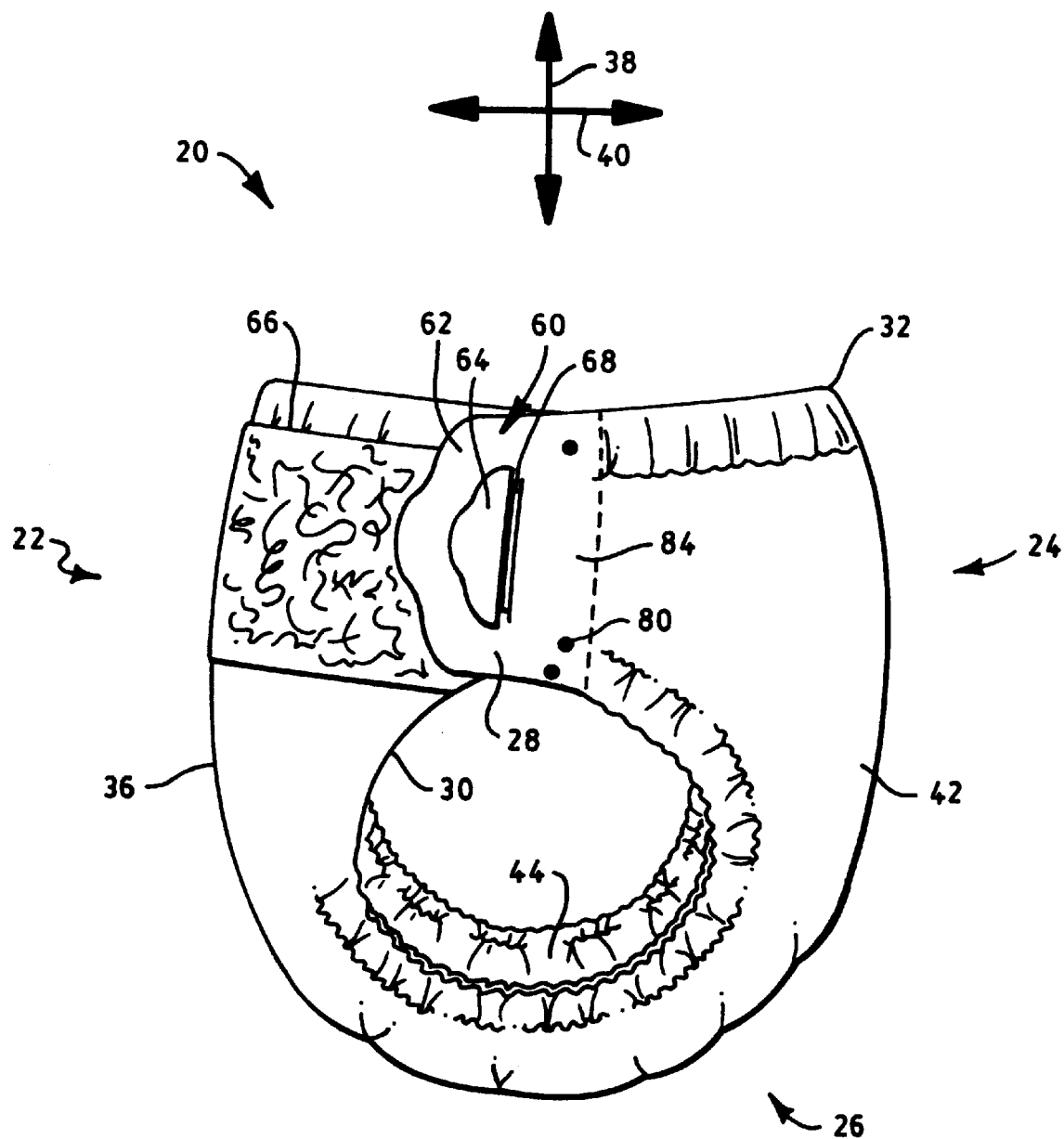
FIG. 1 representatively shows a side view of an example of a prefastened disposable absorbent article according to the present invention.
Figure 2:
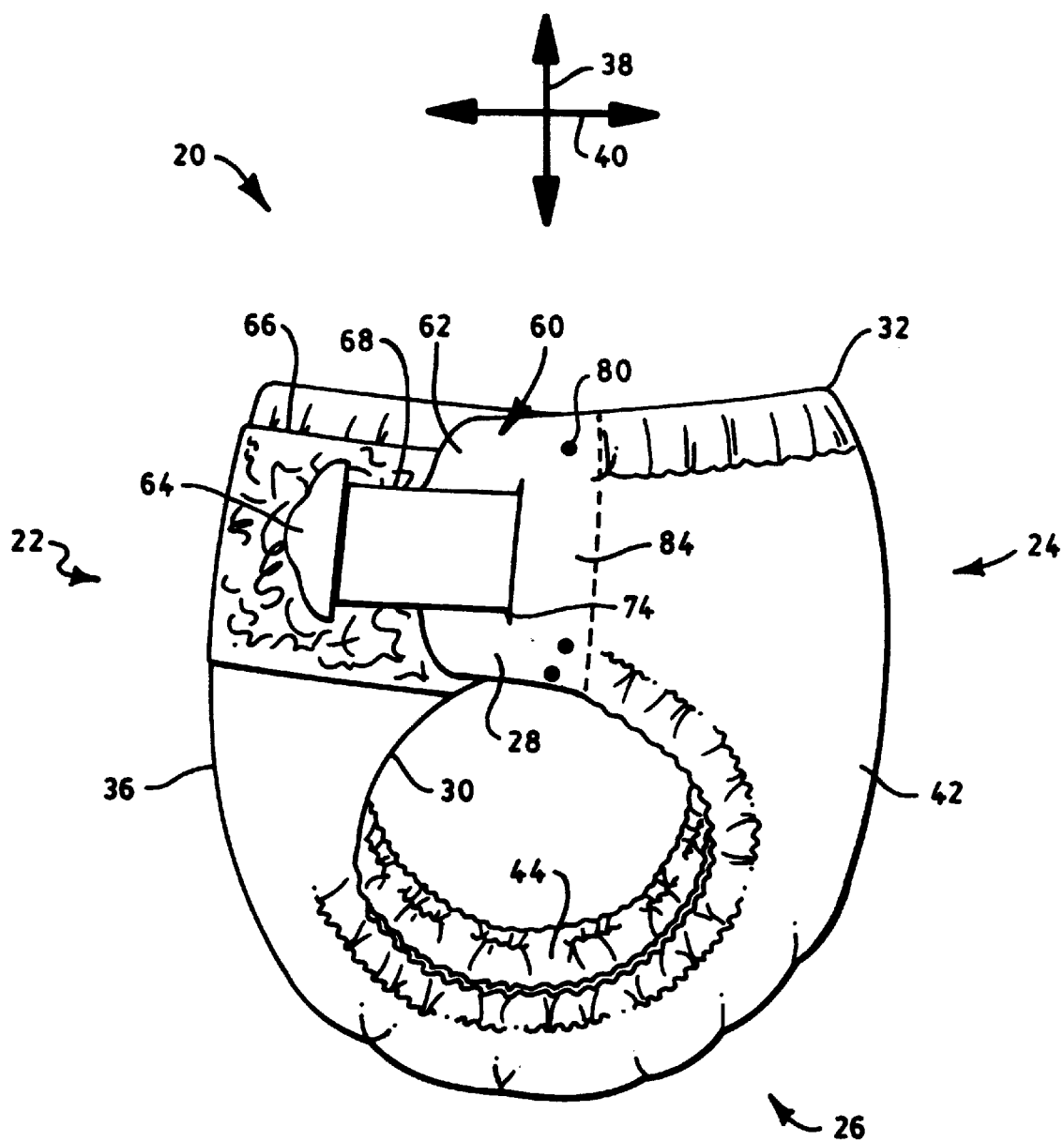
FIG. 2 representatively shows a side view of the disposable absorbent article of FIG. 1 wherein the secondary fasteners have been extended and engaged to conform the waist regions of the article to the waist of the wearer after the article has been pulled on over the hips of the wearer.
Figure 3:
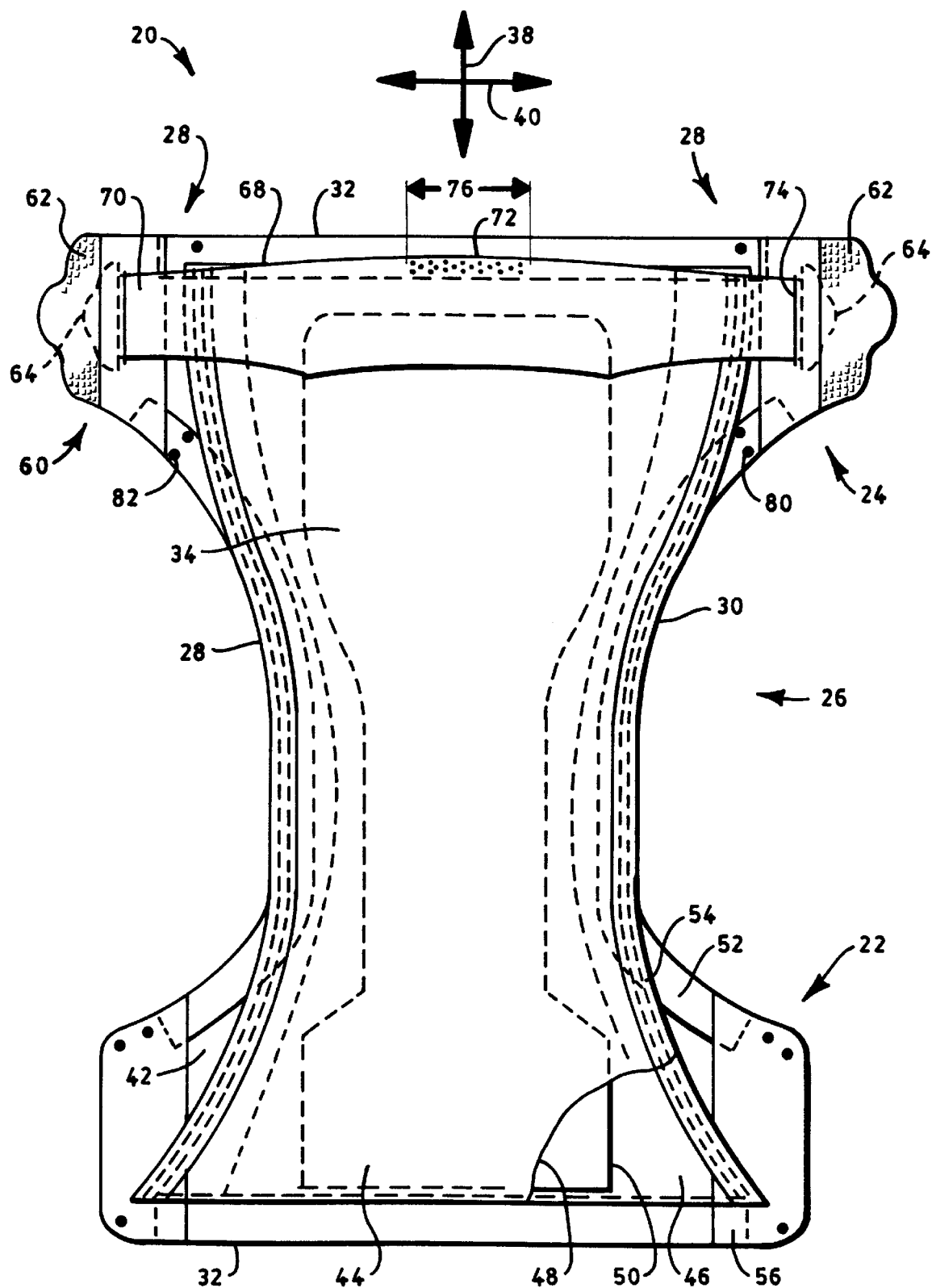
FIG. 3 representatively shows a plan view of the disposable absorbent article of FIG. 1 in an unfastened, stretched and laid flat condition with the surface of the article which contacts the wearer facing the viewer.
Figure 4:
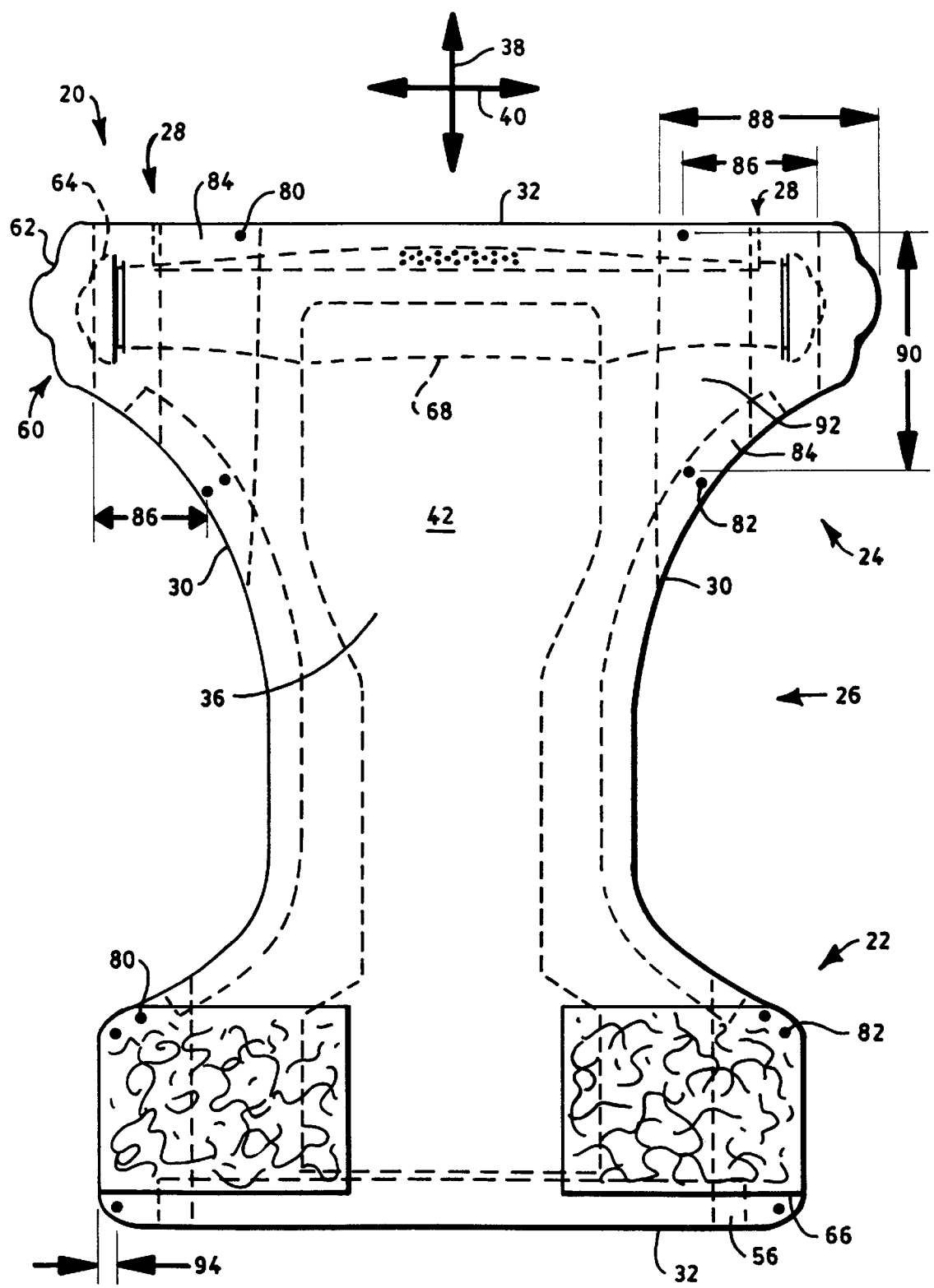
FIG. 4 representatively shows a plan view of the disposable absorbent article of FIG. 1 in an unfastened, stretched and laid flat condition with the surface of the article which contacts the wearer's clothing facing the viewer.

FIGS. 1 and 2 representatively illustrate an example of a prefastened disposable diaper, as generally indicated at 20, according to the present invention. FIGS. 3 and 4 representatively illustrate the diaper of FIG. 1 in an unfastened, stretched and laid flat condition. As representatively illustrated in FIGS. 1–4, the diaper 20 defines a front waist region 22, a back waist region 24, a crotch region 26 which extends between and connects the front and back waist regions 22 and 24 and a pair of laterally opposed ear regions 28 integral with or connected to the back waist region 24. The diaper 20 further defines a pair of laterally opposed side edges 30, a pair of longitudinally opposed waist edges 32, an interior surface 34 which is configured to contact the wearer, an outer surface 36 opposite the interior surface 34, a longitudinal direction 38 and a lateral direction 40.

The front waist region 22 comprises the portion of the diaper 20 which, when worn, is positioned on the front of the wearer while the back waist region 24 comprises the portion of the diaper 20 which, when worm, is positioned on the back of the wearer. The crotch region 26 of the diaper 20 comprises the portion of the diaper 20 which, when worm, is positioned between the legs of the wearer and covers the lower torso of the wearer. The ear regions 28 comprise the portions of the diaper which, when worm, are positioned on the side hip areas of the wearer. The laterally opposed side edges 30 of the diaper 20 generally define leg openings which may be curvilinear. The waist edges 32 of the diaper 20 are configured to encircle the waist of the wearer when worn and provide a waist opening when fastened which defines a waist perimeter dimension.

The illustrated diaper 20 includes an outer cover 42, an absorbent chassis 44, and a multi-functional fastening system 60. The fastening system 60 may include a pair of primary fasteners 62, a pair of secondary fasteners 64 and a pair of laterally opposed passive side bonds 80 and 82. The absorbent chassis 44 is configured to contain and/or absorb any body exudates discharged from the wearer. Whereas, the outer cover 42 and multifunctional fastening system 60 are configured to maintain the diaper 20 about the waist of the wearer, conceal the absorbent chassis 44 from view, and provide a garment-like appearance. The diaper 20 may further include leg elastics 52, containment flaps 54 and waist elastics 56 as are known to those skilled in the art. It should be recognized that individual components of the diaper 20 may be optional depending upon the intended use of the diaper 20.

The outer cover 42 of the diaper 20 may suitably be composed of a material which is either liquid permeable or liquid impermeable. Since the absorbent chassis 44 of the different aspects of the present invention is designed to contain the body exudates discharged from the wearer, it is generally not necessary that the outer cover 42 be liquid impermeable. For example, the outer cover 42 may include various woven or nonwoven materials such as spunbond material, meltblown material, cotton material, rayon material or combinations thereof such as a spunbond-meltblown-spunbond (SMS) laminate material.

The outer cover 42 may otherwise be at least partially liquid impermeable to further prevent any leakage of body exudates. For example, a typical outer cover 42 can be manufactured from a thin plastic film or other flexible liquid-impermeable material. In a particular aspect, the outer cover 42 may be formed from a polyethylene film having a thickness of from about 0.012 millimeter (0.5 mil) to about 0.051 millimeter (2.0 mils). The outer cover 42 may also be formed of a woven or nonwoven fibrous web layer which has been totally or partially constructed or treated to impart a desired level of liquid impermeability to selected regions. Further, the outer cover 42 may optionally be composed of a micro-porous "breathable" material which permits vapors to escape from the diaper 20 while still preventing liquid exudates from passing through the outer cover 42. Still further, the outer cover 42 may be an elasticized material such as a stretch-thermal laminate (STL), neck-bonded laminate (NBL), or stretch-bonded laminate (SBL) material. Methods of making such materials are well known to those skilled in the art and described in U.S. Pat. No. 4,663,220 issued May 5, 1987 to Wisneski et al., U.S. Pat. No. 5,226,992 issued Jul. 13, 1993 to Mormon, and European Patent Application No. EP 0 217 032 published on Apr. 8, 1987 in the names of Taylor et al., the disclosures of which are hereby incorporated by reference.

If it is desired to present the outer cover 42 with a more clothlike feeling, the outer cover 42 may comprise a polyethylene film having a nonwoven web laminated to the outer surface thereof, such as a spunbond web of polyolefin fibers. For example, a polyethylene film having a thickness of about 0.015 millimeter (0.6 mil) may have thermally laminated thereto a spunbond web of polyolefin fibers, which fibers have a thickness of about 1.5 to 2.5 denier per filament, which nonwoven web has a basis weight of about 24 grams per square meter (0.7 ounce per square yard). The outer cover 42 may otherwise be a stretch-thermal laminate (STL) material which includes a film layer positioned between two spunbond layers and which has a basis weight of about 70–75 grams per square meter. The film layer may be composed of meltblown polypropylene fibers and the spunbond layers may be composed of polypropylene fibers. The outer cover 42 may also include bicomponent fibers such as polyethylene/polypropylene bicomponent fibers. Methods of forming such clothlike outer covers are known to those skilled in the art.

The absorbent chassis 44 of the diaper 20 is suitably connected to the outer cover 42 to provide the disposable diaper 20. The absorbent chassis 44 may be connected to the outer cover 42 in manners well known to those skilled in the art. For example, the absorbent chassis 44 may be bonded to the outer cover 42 using adhesive, thermal or ultrasonic bonding techniques known to those skilled in the art. Alternatively, the absorbent chassis 44 may be connected to the outer cover 42 using conventional fasteners such as buttons, hook and loop type fasteners, adhesive tape fasteners, and the like. The other components of the diaper 20 may be suitably connected together using similar means.

Desirably, the absorbent chassis 44 is connected to the outer cover 42 only at or adjacent the waist edges 32 of the outer cover 42 thereby creating a front attached portion, a back attached portion and an unattached portion which extends between and connects the attached portions. The unattached portion of the absorbent chassis 44 remains substantially unattached to the outer cover 42 and is generally configured to fit between the legs of the wearer and at least partially cover the lower torso of the wearer when in use. As a result, the unattached portion is generally the portion of the absorbent chassis 44 which is configured to initially receive the body exudates from the wearer. Thus, the absorbent chassis 44 is connected to the outer cover 42 in such a manner to secure the chassis 44 in place while not adversely restricting the movement of the outer cover 42 in use. Alternatively, the absorbent chassis 44 may be attached to the outer cover 42 along the entire longitudinal length of the absorbent chassis 44 or any portion thereof or along only the outer periphery of the absorbent chassis 44.

As representatively illustrated in FIG. 3, the absorbent chassis 44 according to the present invention may include a backsheet 46, a bodyside liner 48 which is connected to the backsheet 46 in a superposed relation, and an absorbent core 50 which is located between the bodyside liner 48 and the backsheet 46. In alternative configurations wherein the outer cover 42 is at least partially resistant to the flow of liquids therethrough, the backsheet 46 may optionally be omitted from the absorbent chassis 44.

The absorbent chassis 44 is generally conformable and capable of absorbing and retaining body exudates. The absorbent chassis 44 may have any of a number of shapes and sizes. For example, as representatively illustrated in FIG. 3, the absorbent chassis 44 may be rectangular, I-shaped or T-shaped. The size and absorbent capacity of the absorbent chassis 44 should be compatible with the size of the intended wearer and the fluid loading imparted by the intended use of the diaper 20. Typically, it is desirable that the absorbent chassis 44 have an absorbent capacity of at least about 300 grams of urine. It is generally preferred that the absorbent chassis 44 be narrower in the crotch region 26 than in the waist regions 22 and 24. It has been found that the absorbent chassis 44 of the present invention is particularly useful when the width dimension in the crotch region 26 is from about 2.5 to about 10.2 centimeters (1.0 to about 4.0 inches), desirably no more than about 7.6 centimeters (3.0 inches) and more desirably no more than about 5.1 centimeters (2.0 inches). The narrow crotch width dimension of the absorbent chassis 44 allows the absorbent chassis 44 to better fit between the legs of the wearer.

The bodyside liner 48 of the absorbent chassis 44, as representatively illustrated in FIG. 3, suitably presents a bodyfacing surface which is intended to be worn adjacent the body of the wearer and is compliant, soft feeling and nonirritating to the wearer's skin. Further, the bodyside liner 48 may be less hydrophilic than the absorbent core 50, to present a relatively dry surface to the wearer, and may be sufficiently porous to be liquid permeable, permitting liquid to readily penetrate through its thickness. A suitable bodyside liner 48 may be manufactured from a wide selection of web materials, such as porous foams, reticulated foams, apertured plastic films, natural fibers (for example, wood or cotton fibers), synthetic fibers (for example, polyester or polypropylene fibers), or a combination of natural and synthetic fibers. The bodyside liner 48 is suitably employed to help isolate the wearer's skin from fluids held in the absorbent core 50 of the absorbent chassis 44.

Various woven and nonwoven fabrics can be used for the bodyside liner 48. For example, the bodyside liner may be composed of a meltblown or spunbonded web of polyolefin fibers. The bodyside liner may also be a bonded-carded web composed of natural and/or synthetic fibers. The bodyside liner may be composed of a substantially hydrophobic material, and the hydrophobic material may, optionally, be treated with a surfactant or otherwise processed to impart a desired level of wettability and hydrophilicity. In a particular embodiment of the present invention, the bodyside liner 48 comprises a nonwoven, spunbond, polypropylene fabric composed of about 2.8–3.2 denier fibers formed into a web having a basis weight of about 22 grams per square meter and a density of about 0.06 grams per cubic centimeter. The fabric may be surface treated with about 0.28 weight percent of a surfactant commercially available from Rohm and Haas Co. under the trade designation Triton X-102.

The backsheet 46 of the absorbent chassis 44, as representatively illustrated in FIG. 3, may suitably be composed of a material which is either liquid permeable or liquid impermeable. It is generally preferred that the backsheet 46 be formed from a material which is substantially impermeable to fluids. A typical backsheet can be manufactured from a thin plastic film or other flexible liquid-impermeable material. For example, the backsheet 46 may be formed from a polyethylene film having a thickness of from about 0.012 millimeter (0.5 mil) to about 0.051 millimeter (2.0 mils). The backsheet 46 may also comprise a film layer having a nonwoven web laminated to the outer surface thereof, such as a spunbond web of polyolefin fibers. The backsheet 46 may also be constructed of a material which is similar to the material described above as being suitable for the outer cover 42. Further, the backsheet 46 may be formed of a woven or nonwoven fibrous web layer which has been totally or partially constructed or treated to impart a desired level of liquid impermeability to selected regions that are adjacent or proximate the absorbent core 50. Still further, the backsheet 46 may optionally be composed of a microporous "breathable" material which permits vapors to escape from the absorbent co re 50 while still preventing liquid exudates from passing through the backsheet 46. For example, the backsheet 46 may include a breathable polyethylene film material commercially available from Exxon Chemical Patents, incorporated, a business having offices located in Linden, N.J., under the trade designation EXXAIRE. In such a configuration, it is desirable that the outer cover 42 also comprise such a breathable material.

The bodyside liner 48 and backsheet 46 are generally adhered to one another so as to for m a pocket in which the absorbent core 50 is located to provide the absorbent chassis 44. The bodyside liner 48 and backsheet 46 may be adhered directly to each other around the outer periphery of the absorbent chassis 44 by any means known to those skilled in the art such as adhesive bonds, sonic bonds or thermal bonds. For example, a uniform continuous layer of adhesive, a patterned layer of adhesive, a sprayed or meltblown pattern of adhesive or an array of lines, swirls or spots of adhesive may be used to affix the bodyside liner 48 to the backsheet 46. It should be noted that both the bodyside liner 48 and the backsheet 46 need not extend completely to the outer periphery of the absorbent chassis 44. For example, the backsheet 46 may extend to the outer periphery of the absorbent chassis 44 while the bodyside liner 48 may be attached to the backsheet 46 inboard of the outer periphery of the absorbent chassis 44, or more towards the longitudinal centerline 38 of the diaper 20. In alternative configurations, especially wherein the backsheet 46 is omitted, the bodyside liner 48 may be suitably adhered directly to the absorbent core 50 or to the outer cover 42.

The absorbent core 50, as representatively illustrated in FIG. 3, is positioned between the bodyside liner 48 and the backsheet 46 to form the absorbent chassis 44. The absorbent core 50 is desirably conformable and capable of absorbing and retaining body exudates. The absorbent core 50 may have any of a number of shapes and sizes. For example, the absorbent core may be rectangular, I-shaped or T-shaped. It is generally preferred that the absorbent core 50 be narrower in the crotch region 26. The size of the absorbent core 50 should be compatible with the size of the intended wearer and the desired absorbent capacity of the absorbent chassis 44.

The absorbent core 50 of the absorbent chassis 44 may suitably comprise various types of wettable, hydrophilic fibrous materials. Examples of suitable materials indude naturally occurring organic fibers composed of intrinsically wettable material, such as cellulosic fibers; synthetic fibers composed of cellulose or cellulose derivatives, such as rayon fibers; inorganic fibers composed of an inherently wettable material, such as glass fibers; synthetic fibers made from inherently wettable thermoplastic polymers, such as particular polyester and polyamide fibers; and synthetic fibers composed of a nonwettable thermoplastic polymer, such as polypropylene fibers, which have been hydrophilized by appropriate means known to those skilled in the art. The absorbent core 50 may also comprise selected blends of the various types of fibers mentioned above.

In a particular aspect of the invention, the absorbent core 50 may include a matrix of hydrophilic fibers, such as a web of cellulosic fibers, mixed with particles of a high-absorbency material such as that commonly known as superabsorbent material. As used herein, the term "high-absorbency material" refers to materials that are capable of absorbing at least 10 times their own weight in liquid. In a particular embodiment, the absorbent core 50 comprises a mixture of superabsorbent hydrogel-forming particles and wood pulp fluff. The wood pulp fluff may be exchanged with synthetic, polymeric, meltblown fibers or with a combination of meltblown fibers and natural fibers. The high-absorbency material may be substantially homogeneously mixed with the hydrophilic fibers or may be nonuniformly mixed. The high-absorbency material may also be arranged in a generally discrete layer within the matrix of hydrophilic fibers. Alternatively, the absorbent core 50 may comprise a laminate of fibrous webs and high-absorbency material or other suitable means of maintaining a high-absorbency material in a localized area.

The high-absorbency material can be selected from natural, synthetic and modified natural polymers and materials. The high-absorbency materials can be inorganic materials, such as silica gels, or organic compounds, such as crosslinked polymers. The term "crosslinked" refers to any means for effectively rendering normally water-soluble materials substantially water insoluble but swellable. Such means can include, for example, physical entanglement, crystalline domains, covalent bonds, ionic complexes and associations, hydrophilic associations such as hydrogen bonding, and hydrophobic associations or Van der Waals forces.

Examples of synthetic, polymeric, high-absorbency materials include the alkali metal and ammonium salts of poly (acrylic acid) and poly(methacrylic acid), poly (acrylamides), poly(vinyl ethers), maleic anhydride copolymers with vinyl ethers and alpha-olefins, poly(vinyl pyrolidone), poly(vinyl morpholinone), poly(vinyl alcohol), and mixtures and copolymers thereof. Further polymers suitable for use in the absorbent core include natural and modified natural polymers, such as hydrolyzed acrylonitrile-grafted starch, acrylic acid grafted starch, methyl cellulose, carboxymethyl cellulose, hydroxypropyl cellulose, and the natural gums, such as alginates, xanthum gum, locust bean gum, and the like. Mixtures of natural and wholly or partially synthetic absorbent polymers can also be useful in the present invention.

The high-absorbency material may be in any of a wide variety of geometric forms. As a general rule, it is preferred that the high-absorbency material be in the form of discrete particles. However, the high-absorbency material may also be in the form of fibers, flakes, rods, spheres, needles, or the like. Conglomerates of particles of high-absorbency material may also be used. An example of a superabsorbent polymer suitable for use in the present invention is a superabsorbent polymer designated IM5000 which is commercially available from Hoechst-Celanese, a business having offices in Portsmouth, Va. Other suitable high-absorbency materials may include superabsorbent polymers which are commercially available from Dow Chemical Corp., a business having offices in Midland, Mich.

As a general rule, the high-absorbency material is present in the absorbent core 50 of the present invention in an amount of from about 5 to about 95 weight percent and desirably from about 10 to about 60 weight percent based on the total weight of the absorbent core 50. The distribution of the high-absorbency material within the different portions of the absorbent core 50 can vary depending upon the intended end use of the absorbent core 50.

As representatively illustrated in FIG. 3, the absorbent chassis 44 of the disposable diaper 20 may include a pair of containment flaps 54 which are configured to provide a barrier to the lateral flow of body exudates. The containment flaps 54 may be located along the laterally opposed side edges of the absorbent chassis 44. Each containment flap 54 typically defines an unattached edge which is configured to maintain an upright, perpendicular configuration in at least the crotch region 26 of the diaper 20 to form a seal against the wearer's body. The containment flaps 54 may extend longitudinally along the entire length of the absorbent chassis 44 or may only extend partially along the length of the absorbent chassis 44. When the containment flaps 54 are shorter in length than the absorbent chassis 44, the containment flaps 54 can be selectively positioned anywhere along the side edges of the absorbent chassis 44. In a particular aspect of the invention, the containment flaps 54 extend along the entire length of the absorbent chassis 44 to better contain the body exudates.

Such containment flaps 54 are generally well known to those skilled in the art. For example, suitable constructions and arrangements for containment flaps 54 are described in U.S. Pat. No. 4,704,116 issued Nov. 3, 1987, to K. Enloe the disclosure of which is hereby incorporated by reference.

The disposable diaper 20 of the different aspects of the present invention may further include elastics at the waist edges 32 and side edges 30 of the diaper 20 to further prevent the leakage of body exudates and support the absorbent chassis 44. For example, as representatively illustrated in FIG. 3, the diaper 20 of the present invention may include a pair of leg elastic members 52 which are connected to the laterally opposed side edges 30 in the crotch region 26 of the diaper 20 and a pair of waist elastic members 56 which are connected to the longitudinally opposed waist edges 32 of the diaper 20. The leg elastics 52 and waist elastics 56 are generally adapted to fit about the legs and waist of a wearer in use to maintain a positive, contacting relationship with the wearer to effectively reduce or eliminate the leakage of body exudates from the diaper 20.

Materials suitable for use as the leg elastics 52 and waist elastics 56 are well known to those skilled in the art. Exemplary of such materials are sheets or strands or ribbons of a polymeric, elastomeric material which are adhered to the edges 30 and 32 of the diaper 20 in a stretched position, or which are attached to the edges 30 and 32 while the edges are pleated, such that elastic constrictive forces are imparted to the edges 30 and 32. The leg elastics may also include such materials as polyurethane, synthetic and natural rubber. In a particular aspect of the invention, the elastics may be composed of individual strands of 620 decitex LYCRA which are commercially available from E. I. DuPont de Nemours Co. When individual strands of elastic are used, the waist and leg elastics may include any suitable number of elastic strands to provide containment of the body exudates. For example, the leg elastics 52 may include from about 1 to about 10 elastic strands. The elastics 52 and 56 may be elongated prior to being attached to the diaper 20. For example, the elastics 52 and 56 may be elongated at least about 150 percent and desirably from about 200 to about 500 percent before being attached such that the elastics gather the edges 30 and 32 of the diaper 20 when relaxed. The elastics 52 and 56 may be joined to the diaper 20 by any means known to those skilled in the art. For example, adhesive, thermal or ultrasonic bonding techniques or a combination thereof may be used to join the elastics to the edges of the diaper 20. A suitable adhesive includes Findley H-2096 hot melt adhesive which is commercially available from Findley Adhesives, Inc.

The absorbent article of the different aspects of the present invention further includes a multifunctional fastening system 60 for securing the absorbent article about the waist of the wearer. The multifunctional fastening system includes fasteners located on one of the waist regions 22 and 24 of the diaper 20 which are configured to releasably engage the opposite waist region of the diaper 20 to maintain the diaper about the waist of the wearer. The use of fasteners which are refastenable or releasably engageable allows for ease of securing and removing the diaper 20 from the waist of the wearer.

A suitable multi-functional fastening system is described in U.S. patent application Ser. No. 08/907,585 entitled "A MULTI-FUNCTIONAL FASTENER FOR DISPOSABLE ABSORBENT ARTICLES" and filed Aug. 8, 1997 in the name of J. D. Suprise, the disclosure of which is hereby incorporated by reference. As described in the referenced application and representatively illustrated in FIG. 14, the multi-functional fastening system 60 of the present invention may include a pair of primary fasteners 62 which are located on the side edges 30 of the diaper 20 in the back waist region 24 of the diaper 20. In such a configuration, the primary fasteners 62 are configured to encircle the hips of the wearer and engage the outer surface 36 of the front waist region 22 of the diaper 20 to maintain the diaper 20 on the wearer. Alternatively, the primary fasteners 62 may be located on the front waist region 22 and may be configured to releasably engage the outer surface 36 of the back waist region 24 of the diaper 20.

Desirably, the primary fasteners 62 are releasably engageable directly with the outer surface of the outer cover 42 of the diaper 20 to provide improved ease of fastening. Alternatively, as representatively illustrated in FIG. 4, the disposable diaper 20 of the present invention may further include an attachment panel 66 located on the outer cover 42 in one of the waist regions 22 and 24 of the diaper 20. In such a configuration, the primary fasteners 62 are releasably engageable with the attachment panel 66 to maintain the diaper 20 about the waist of the wearer. When the primary fasteners 62 are releasably engaged, the side edges 30 of the diaper 20 define leg openings which are configured to encircle the legs of the wearer and the waist edges 32 define a waist opening which is configured to encircle the waist of the wearer. As illustrated in FIG. 4, the attachment panel 66 may include two separate panels located along the opposite side edges in one of the waist regions 22 and 24 of the diaper 20. Alternatively, the attachment panel 66 may include a single piece of material which extends substantially across the respective waist region of the diaper 20.

In the different aspects of the present invention, the primary fasteners 62 are releasably engaged with the outer surface of the opposite waist region 22 and 24 of the diaper 20 before the diaper 20 is placed on the wearer to provide a prefastened diaper. In such a configuration, the prefastened diaper 20 can be pulled on or off over the legs and hips of the wearer. If the diaper 20 becomes soiled during use, the primary fasteners 62 can be disengaged to easily remove the diaper 20 from the waist of the wearer with reduced risk of undesirably soiling the clothes or legs of the wearer. Thus, in such a configuration, the diaper 20 of the different aspects of the present invention can be configured to be pulled on or off over the hips of the wearer such as conventional training pants and can be readily removed by disengaging the fasteners similar to conventional diaper articles.

The multi-functional fastening system 60 on the disposable diaper 20 of the present invention may further include at least one secondary fastener to provide improved securement of the diaper 20 about the waist of the wearer when the primary fasteners 62 are releasably engaged. The secondary fastener of the present invention is configured to further conform the waist regions 22 and 24 of the diaper 20 to the waist of the wearer. Alternatively, in embodiments wherein the secondary fasteners are omitted, the primary fasteners 62 are capable of being reengaged after the diaper is pulled on to further conform the waist regions of the diaper to the waist of the wearer.

The diaper 20 in the illustrated embodiments includes a pair of secondary fasteners 64 which are located on the side edges 30 in one of the waist regions 22 and 24 of the diaper 20. The secondary fasteners 64 are configured to encircle the hips of the wearer and engage the outer surface 36 in the opposite waist region 22 and 24 of the diaper 20. The secondary fasteners 64 may be located on the side edges 30 of the diaper 20 in the back waist region 24 of the diaper 20. In such a configuration, the secondary fasteners 64 are also configured to encircle the hips of the wearer and engage the outer surface 36 of the front waist region 22 of the diaper 20 to maintain the diaper 20 on the wearer. Alternatively, the secondary fasteners 64 may be located on the front waist region 22 and may be configured to releasably engage the outer surface 36 of the back waist region 24 of the diaper 20.

Desirably, the secondary fasteners 64 are releasably engageable directly with the outer surface of the outer cover 42 of the diaper 20 to provide improved ease of fastening. Alternatively, as described above and representatively illustrated in FIGS. 1–4, the diaper 20 of the present invention may further include an attachment panel 66 located on the outer cover 42 in one of the waist regions 22 and 24 of the diaper 20. In such a configuration, the secondary fasteners 64 may also be releasably engageable with the attachment panel 66 to maintain the diaper 20 about the waist of the wearer.

The use of such a secondary fastener has been found to be particularly desirable when the primary fasteners 62 are releasably engaged with the respective waist region of the diaper 20 to provide a prefastened diaper which can be pulled on over the legs and hips of the wearer. In such a configuration, the waist opening of the diaper 20 when the primary fasteners 62 are engaged must be sufficient to allow the prefastened diaper to be pulled over the hips of the wearer. However, the circumference of the waist of the wearer is typically less than the circumference around the hips of the wearer. Thus, the waist opening of the prefastened diaper may not conform to the waist of the wearer which may undesirably result in leaks. In such a configuration, the secondary fastener 64 of the diaper 20 of the present invention is configured to conform the waist regions of the diaper 20 to the wearer by reducing the waist perimeter dimension of the diaper 20 after the prefastened diaper is pulled on the wearer. Thus, the care giver is not required to reposition the primary fasteners 62 to conform the waist regions 22 and 24 to the waist of the wearer. As a result, when the diaper 20 is to be removed from the wearer, the care giver may simply disengage the secondary fastener 64 if necessary and pull the prefastened diaper down over the hips and legs of the wearer without having to reposition the primary fasteners 62. Alternatively, the care giver may disengage both the secondary and primary fasteners 64 and 62 to remove the diaper in a manner similar to conventional diapers.

In such configurations, the secondary fasteners 64 are intended to maintain the diaper 20 in a close conforming fit about the waist of the wearer to reduce the leakage of body exudates when in use. The primary fasteners 62 are intended to maintain the front and back waist regions 22 and 24 of the diaper 20 connected in such a manner that the diaper 20 can be pulled on or off over the hips of the wearer after the secondary fasteners 64 have been disengaged. The secondary fasteners 64 may also be selectively disengaged to facilitate inspection of the diaper 20 to determine if it has been soiled. The primary fasteners 62 can also provide a "childproofing function" by maintaining the diaper 20 at least partially secured about the waist of the wearer if the wearer disengages the secondary fasteners 64.

The secondary fasteners 64 may also provide improved fit when the diaper 20 is applied from an unfastened configuration similar to conventional diapers. For example, upon the initial fastening about the wearer, the primary fasteners 62 may be difficult to locate correctly due to the activity of the wearer. Thus, in such situations, the secondary fasteners can be used to provide a better conforming fit after the primary fasteners 62 have been engaged.

Suitable fasteners are well known to those skilled in the art and can include adhesive tape tab fasteners, cohesives, magnetics, hook and loop fasteners, mushroom fasteners, snaps, pins, belts and the like, and combinations thereof. For example, as representatively illustrated in FIG. 3, the primary fasteners 62 and secondary fasteners 64 may be hook type fasteners and the outer cover 42 or attachment panel 66 may be configured to function as a complimentary loop type fastener. Desirably, the fasteners 62 and 64 are hook type fasteners which are releasably engageable directly with the outer cover 42. Such an arrangement provides the ability to vary the size of the waist opening in very small increments over a wide range to fit the waist of the wearer. The fasteners may have any shape and size which provides the desired fastening of the diaper 20 about the waist of the wearer. It is further desirable that the outer surface of the secondary fasteners 64 provide a visual cue to the care giver as to their location. For example, in one embodiment, the secondary fasteners 64 are of a different color than the outer surface of the diaper 20 to enable the care giver to easily determine the location of the secondary fasteners 64.

In the illustrated embodiments, the primary fasteners 62 are attached directly to the side edges 30 of the diaper 20 in one of the waist regions 22 and 24. The primary fasteners 62 may be adhered to the side edges 30 by any means known to those skilled in the art such as adhesive bonds, sonic bonds or thermal bonds.

The secondary fasteners 64 may suitably be secured to the diaper 20 in any manner which provides the desired improved securement and conformance of the waist regions 22 and 24 of the diaper 20 about the waist of the wearer after the diaper 20 has been pulled on over the hips of the wearer. For example, as representatively illustrated in FIGS. 3 and 4, the diaper 20 of the different aspects of the present invention may further include a belt segment 68 located in one of the waist regions 22 and 24 of the diaper 20. The illustrated belt segment 68 defines a pair of laterally opposed end portions 70 and an attached portion 72 which is secured to the respective waist region 22 and 24 of the diaper 20. The secondary fasteners 64 are connected to the end portions 70 of the belt segment 68. In such a configuration, the end portions 70 of the belt segment 68 are configured to encircle the hips of the wearer such that the secondary fasteners 64 can releasably engage the opposite waist region to provide the improved fit of the diaper on the wearer after the diaper 20 has been pulled on over the legs and hips of the wearer.

To provide the improved fit about the waist of the wearer without adversely affecting the appearance of the outer cover 42 of the diaper 20, the majority of the length of the belt segment 68 desirably is positioned along the interior surface 34 of the diaper 20 in the respective waist region 22 and 24. In such a configuration as representatively illustrated in FIG. 3, the diaper 20 further includes a pair of slots 74 through which the end portions 70 of the belt segment 68 slidably extends. Thus, the end portions 70 of the belt segment 68 and the secondary fasteners 64 are located on the outer surface 36 of the diaper and the remaining portion of the belt segment 68 extends through to and along the interior surface 34 of the diaper 20 between the diaper and the wearer. As illustrated, the secondary fasteners 64 are desirably configured to releasably engage the outer surface 36 of the diaper 20 adjacent the slots 68 for improved control and ease of fastening.

The slots 74 may be provided by any means known to those skilled in the art. For example, the slots 74 may be provided by cutting the diaper 20 after it has been assembled together. Alternatively, the slots 74 may be provided by adding a segment of material to the side edges 30 of the diaper 20 which extends laterally outward from the side edges 30 while only attaching the segment of material to the side edges at its longitudinal ends. In such a configuration, the segment of material provides a slot between the side edge of the diaper and the segment of material for improved manufacturability.

In such a configuration, a portion of the belt segment 68 between the slots 74 is secured to the interior surface 34 of the diaper 20 to provide an attached portion 72. The attached portion 72 of the belt segment 68 may be secured to the interior surface of the diaper using methods known to those skilled in the art such as adhesive, sonic or thermal bonding. Desirably, the attached portion 72 defines an attached length 76 as illustrated in FIG. 3 which is less than about 75 percent and more desirably less than about 50 percent of the total length of the belt segment 68. Such an attached length provides sufficient securement of the belt segment to the diaper 20 without adversely affecting the ability of the belt segment to conform to the waist of the wearer to provide the improved fit.

In alternative configurations, the belt segment 68 need not extend all the way through the diaper 20 to the interior surface 34. For example, the majority of the belt segment 68 may extend between the outer cover 42 and the absorbent chassis 44 or between any of the components of the absorbent chassis to further conceal the belt segment 68.

The belt segment 68 may define any length and width which provide the desired improved fastening and fit about the wearer. For example, the belt segment 68 may define a length which is from about 7 to about 35 centimeters and a width which is from about 1 to about 10 centimeters. Desirably, the belt segment 68 defines a length which is slightly less than the width of the diaper 20 at the respective waist region such that the belt segment 68 is slightly elongated to pretension the waist region.

Materials suitable for use as the belt segment 68 of the different aspects of the present invention are similar to those materials described above as being suitable for the outer cover 42. Desirably, the belt segment 68 is made of an elastic material which is capable of elongating at least about 50 percent and more desirably at least about 100 percent to provide improved fit about the waist of the wearer. For example, the belt segment 68 may comprise a neck bonded laminate material which includes a KRATON film material commercially available from the Dow Chemical Company, a business having offices located in Midland, Mich. Alternatively, the belt segment 68 may include portions which include elastic material and portions which include inelastic material. The belt segment 68 may otherwise be made of a latent elastic material which may be elastically activated after the diaper 20 is constructed and before it is worn. In a particular embodiment, the belt segment 68 is made of a latent elastic material as described in U.S. patent application Ser. No. 08/854,934 filed May 13, 1997 and entitled "IMPROVED COMPOSITE ELASTIC MATERIAL AND PROCESS FOR PRODUCING THE SAME", the disclosure of which is hereby incorporated by reference.

The prefastened absorbent article of the different aspects of the present invention further includes a pair of passive side bonds for improved reliability of maintaining the article in the prefastened condition particularly when it is being pulled on or off over the hips of the wearer. For example, as representatively illustrated in FIGS. 1–4, the diaper 20 includes a pair of passive side bonds 80 and 82 which releasably connect an overlapped portion 84 of the back waist region 24 or the opposed ear regions 28 to the front waist region 22 of the diaper 20. In such a configuration, the passive side bonds 80 and 82 assist the fastening system 60 in maintaining the diaper 20 in a prefastened condition as the diaper 20 is pulled up or down over the hips of the wearer. Moreover, the passive side bonds 80 and 82 prevent movement and shifting of the waist regions 22 and 24 and ear regions 28 relative to each other for improved fit and performance. The passive side bonds 80 and 82 also provide improved hip coverage and prevent rollover or folding of the side edges 30 and waist edges 32 of the prefastened diaper 20 as it is pulled over the wearers hips. Such prevention of rollovers and foldovers can reduce the level of contact between the fasteners and the skin of the wearer which can desirably result in reduced skin irritation and redness.

As shown in the illustrated embodiments, the passive side bonds 80 and 82 are located inward of the primary fasteners 62 on the back waist region 24 of the diaper 20. As used herein, the term "inward" refers to a distance in the lateral direction 40 towards the longitudinal centerline 38 of the diaper 20 from the respective element. In such a configuration, the passive side bonds 80 and 82 connect and stabilize the overlapped portion 84 of the back waist region 24 inward of the primary fasteners 62 to the front waist region 22. Desirably, the passive side bonds 80 and 82 connect the overlapped portion 84 of the back waist region 24 to the side edge 30 of the front waist region 22. For example, the passive side bonds 80 and 82 may bond a waist edge 32 and side edge 30 of the back waist region 24 to the side edge 30 of the front waist region 22. In such a configuration, the passive bonds 80 and 82 assist in preventing the side edges 30 and waist edges 32 from rolling over as the diaper 20 is pulled on.

As illustrated in FIG. 4, the overlapped portion 84 of the back waist region 24 defines an overlap distance 88 which is the distance between the respective side edges 30 of the front and back waist regions 22 and 24 when the diaper is prefastened. The overlap distance 88 is important to ensure that a good seal is provided around the legs and waist of the wearer. Moreover, the greater the overlap distance 88, the further inward the passive bonds 80 and 82 can be located which can provide improved reduction in the relative movement between the front and back waist regions 22 and 24 and improved hip coverage during use. The larger overlap distance 88 is also desirable in the processing of the diaper 20 since the overlapped portion 84 is typically folded over and attached to the opposite waist region after the side bonds 80 and 82 are formed. To provide such improved fit and performance, it is desirable that the overlap distance 88 be at least about 2.0 centimeters and more desirably at least about 4.0 centimeters. As illustrated in FIG. 4, the passive bonds 80 and 82 may also be located on the opposite waist region a distance 94 inward form the side edge 30 of about 0.2 to about 2.5 centimeters for improved attachment and performance.

In a particular embodiment, the overlapped portions 84 of the back waist region 24 are connected by the passive bonds 80 and 82 to the front waist region 22 along their edges 30 and 32 but remain unconnected by the passive bonds 80 and 82 to the front waist region 22 between the edges 30 and 32. In such an embodiment, the passive bonds 80 and 82 are not continuous along their length in the longitudinal direction 38. For example, as representatively illustrated in FIG. 4, the passive bonds 80 and 82 on each side of the back waist region 24 may further define an unattached distance 90 in the longitudinal direction 38 between the respective bond points of at least about 1.0 centimeters and desirably at least about 2.0 centimeters. Such an arrangement is particularly useful when the fastening system 60 of the diaper 20 includes the belt segment 68 described above such that the belt segment 68 is allowed to freely slide in the sleeve 92 created between the passive bonds 80 and 82.

As illustrated in FIG. 4, the passive side bonds 80 and 82 are located on the back waist region 24 inward from the primary fastener 62 a distance 86 to prevent the relative movement or shifting between the front and back waist regions 22 and 24 with respect to each other. In a particular embodiment, at least one of the bonds of each of the passive side bonds 80 and 82 is located on the back waist region 24 a distance 86 inward of at least about 1.0 centimeters and desirably at least about 2.0 centimeters. When the distance 86 is less than the values set forth above, the front and back waist regions 22 and 24 may undesirably shift with respect to each other during the application or use of the diaper 20. Such shifting of the respective waist regions 22 and 24 of the diaper 20 can adversely affect the fit of the diaper 20 on the wearer which can undesirably lead to increased leakage.

In certain aspects of the invention, the location of the passive bonds 80 and 82 and the respective distance 86 and overlap distance 88 can be selectively varied to tailor the fit of the diaper 20 for different sized wearers. For example, the location of the bonds 80 and 82 may be varied during the manufacturing process such that the same process can produce prefastened diapers for use in conventional Step 3 or Step 4 sizes.

The passive side bonds 80 and 82 may connect the respective front and back waist regions 22 and 24 in a facing relationship. For example, the passive side bonds 80 and 82 may connect the interior surface 34 of the diaper 20 in the rear waist region 24 to the outer surface 36 of the diaper in the front waist region 22. Alternatively, the passive side bonds 80 and 82 may connect the interior surface 34 of the diaper 20 in the rear waist region 24 to the interior surface 34 of the diaper 20 in the front waist region 22. Such a configuration can lead to improved manufacturability. In such a configuration, the side edges 30 of the front waist region 22 may be folded over when the primary fasteners 62 are engaged.

The passive side bonds 80 and 82 can be provided by any type of bonding such as thermal, adhesive, ultrasonic, cohesive bonding and the like and combinations thereof as are well known to those skilled in the art. The passive side bonds 80 and 82 may otherwise be provided by suitable fasteners as are known to those skilled in the art and described above as being suitable for use as the primary fasteners 62. The passive side bonds 80 and 82 may be discrete point bonds, dashed lines, continuous lines, discontinuous lines and the like or combinations thereof. Moreover, the side bonds 80 and 82 may have any shape such as circular, square, triangular and the like. In a particular embodiment, the passive side bonds 80 and 82 are ultrasonic point bonds for improved manufacturing efficiency.

Methods of incorporating the passive bonds 60 and 62 and making the prefastened diaper 20 of the different aspects of the present invention are known to those skilled in the art. For example, in addition to making the diaper by hand, one of such methods is described in copending U.S. Patent Application entitled "METHOD OF MAKING PREFASTENED DISPOSABLE ABSORBENT ARTICLES" filed herewith in the name of Elsberg et al. and having Attorney Docket No. 13,780, the disclosure of which is hereby incorporated by reference.

The passive side bonds 80 and 82 are configured to assist the primary fasteners 62 in maintaining the diaper 20 in a prefastened configuration as the diaper 20 is pulled on and off over the hips of the wearer and during use. Thus, it is desirable that the passive side bonds 80 and 82 provide adequate shear strength for assisting the primary fasteners 62. In a particular embodiment, the passive side bonds 80 and 82 define a shear strength of at least about 50 grams and desirably at least about 100 grams. For example, the passive side bonds 80 and 82 may define a shear strength of from about 100 to about 4000 grams and desirably from about 500 to about 2000 grams. As used herein, the term "shear strength" refers to the value obtained when subjecting the side bonds to the Shear Strength Test described herein. Shear strength values less than those described above may not prevent the separation of the front and rear waist regions 22 and 24 from each other during the application and use of the diaper 20.

The passive side bonds 80 and 82 are also configured to be readily tearable such that the caregiver can easily pealingly remove the diaper 20 from the wearer after it has been soiled. Thus, it is desirable that the passive side bonds 80 and 82 define a relatively low peak peel strength such that the caregiver can readily disengage the fasteners 62 and 64, break the passive side bonds 80 and 82 and separate the front and back waist regions 22 and 24 to remove the diaper 20 from the waist of the wearer similar to conventional diapers which are not prefastened. For example, in a particular embodiment, the passive side bonds 80 and 82 define a peel strength of no more than about 1500 grams, desirably no more than about 1000 grams, and more desirably no more than about 800 grams. As used herein, the term "peel strength" refers to the value obtained when subjecting the side bonds to the Peel Strength Test described herein. Peel strength values greater than those described above may not be readily tearable and may undesirably result in tearing of other portions of the diaper 20. Desirably, the peel strength of the side bonds 80 and 82 is less than about 50 percent of the peel strength of the primary fasteners 62 and more desirably less than about 20 percent of the peel strength of the primary fasteners 62.

In another aspect, the present invention provides a package of the prefastened disposable diapers described above. The package includes a container such as, for example, a plastic bag, and a plurality of prefastened disposable diapers. As described above, the prefastened diaper 20 induces a pair of primary fasteners 62 and a pair of passive side bonds 80 and 82 located inward from said primary fasteners. Such a package provides diapers which can be reliably pulled on over the legs of the wearer and which can be easily removed from the waist of the wearer after they have been soiled.

The different aspects of the present invention can advantageously provide a prefastened disposable absorbent article which induces the combination of passive side bonds and an adjustable fastening system. The fastening system is prefastened to releasably engage the front and back waist portions to allow the absorbent article to be pulled up or down over the hips of the wearer such as conventional training pants. Moreover, the fastening system can be used to releasably engage and adjust the front and back waist portions of the absorbent article to maintain the absorbent article about the waist of the wearer after the article has been pulled on in a similar manner to conventional diapers. The passive side bonds assist the fastening system in maintaining the article in a prefastened condition as the article is pulled up or down over the hips of the wearer. Moreover, the passive side bonds prevent movement and shifting of the waist portions relative to each other for improved fit and performance. The passive side bonds also prevent the rollover or folding on the side and waist edges of the prefastened absorbent article as it is pulled over the wearers hips.

As a result, the absorbent articles of the present invention are designed to conform to the body of the wearer to effectively contain bodily exudates while still being capable of being reliably pulled up or down over the hips of the wearer to assist in the toilet training of the wearer. Moreover, similar to conventional diapers, the absorbent articles of the present invention can advantageously be applied to and removed from the wearer with relative ease and cleanliness.

Peel Strength Test

This test method is designed to quantify, in grams, the peak strength of the ultrasonic point bonds holding the front waist region of the absorbent article to the rear waist region. The direction of removal (peel), in this application, is that direction in which the fastener material would generally be removed from a substrate when the product is in use. This direction is generally perpendicular to a longitudinal centerline of the product.

Equipment

1. Tensile tester capable of obtaining a peak load and equipped with an appropriate load cell. A suitable tensile testing system is a Sintech Tensile Tester, commercially available from MTS Sintech, Research Triangle Park, N.C., under the trade designation Instron Model 4201 Tensile Tester with Sintech QAD (Quality Assurance Department) Software.
2. Software commercially obtained from MTS Sintech under the trade designation Sintech Testworks™.
3. Pnuematic-action grips commercially available from Instron Corporation, Canton, Mass., under the trade designation "Instron Model 2712-004."
4. 1 by 4 inch grip faces, serrated, commercially available from Instron Corporation, Canton, Mass.
5. Test facility having a temperature of 23±1° C., and a relative humidity of 50±2 percent.

Test Procedure

1. A sample to be tested is conditioned in the test facility for at least 4 hours prior to testing.
2. The load cell is calibrated and the software loaded.
3. The grips are installed on the tensile tester with the jaws closed.
4. The test condition for the tensile tester are set as follows:
   Crosshead speed: 500 millimeters/minute
   Full-scale load: 5 kilograms
   Threshold: 5 percent
   Fail criterion: 95 percent
   Gage length: 50 millimeters
5. The weight of the damp is tared out
6. The primary fastener tab of the fastening element on the back waist region of the article is inserted into the upper jaw such that the edge of the grip face is flush with the inner edge of the hook material.

7. The front waist region of the article is inserted into the lower jaw such that the inner surface of the back waist region and the outer surface of the front waist region form a 180° angle. The lower jaw is closed.
8. The crosshead is started in motion.
9. The peak load of failure is recorded. It is intended that the mode of failure is that the back waist region of the diaper separates from the front waist region of the diaper. Results are rejected if the place of failure is any location other than the ultrasonic point bonds.

Shear Strength Test

This test method is designed to quantify, in grams, the peak dynamic shear strength of the ultrasonic point bonds holding the front waist region of the absorbent article to the rear waist region. The direction of force in this application is generally perpendicular to the longitudinal centerline of the product.

Equipment

1. Tensile tester capable of obtaining a peak load and equipped with an appropriate load cell. A suitable tensile testing system is a Sintech Tensile Tester, commercially available from MTS Sintech, Research Triangle Park, North Carolina, under the trade designation Instron Model 4201 Tensile Tester with Sintech QAD (Quality Assurance Department) Software.
2. Software commercially obtained from MTS Sintech under the trade designation Sintech Testworks™.
3. Pnuematic-action grips commercially available from Instron Corporation, Canton, Mass., under the trade designation "Instron Model 2712-004."
4. 1 by 4 inch grip faces, serrated, commercially available from Instron Corporation, Canton, Mass.
5. Test facility having a temperature of 2±1° C., and a relative humidity of 50±2 percent.

Test Procedure

1. A sample to be tested is conditioned in the test facility for at least 4 hours prior to testing.
2. The load cell is calibrated and the software loaded.
3. The grips are installed on the tensile tester with the jaws closed.
4. The test condition for the tensile tester are set as follows:
   Crosshead speed: 500 millimeters/minute
   Full-scale load: 5 kilograms
   Threshold: 5 percent
   Fail criterion: 95 percent
   Gage length: 50 millimeters
5. The weight of the clamp is tared out.
6. The primary fastener tab of the fastening element on the back waist region of the article is inserted into the upper jaw such that the edge of the grip face is flush with the inner edge of the hook material.
7. The front waist region of the article is inserted into the lower jaw such that the inner surface of the back waist region and the inner surface of the front waist region are facing the same direction and are parallel to one another. The lower jaw is closed.
8. The crosshead is started in motion.
9. The peak load of failure is recorded. It is intended that the mode of failure is that the back waist region of the article separates from the front waist region of the article. Results are rejected if the place of failure is any location other than the ultrasonic point bonds.

While the invention has been described in detail with respect to specific aspects thereof, it will be appreciated that those skilled in the art, upon attaining an understanding of the foregoing, may readily conceive of alterations to, variations of and equivalents to these aspects. Accordingly, the scope of the present invention should be assessed as that of the appended claims and any equivalents thereto.

I claim:

1. A prefastened disposable absorbent article which defines an absorbent, a front waist region, a back waist region, a crotch region which extends between and connects said waist regions and a pair of opposed side edges wherein said prefastened absorbent article comprises:
   a) a pair of primary fasteners which are located on said opposed side edges in one of said waist regions and which overlap and releasably engage said opposite waist region of said absorbent article to provide said prefastened absorbent article; and
   b) a pair of passive side bonds which are located inward of said primary fasteners on said one waist region and which releasably connect an overlapped portion of said one waist region to said opposite waist region to assist in maintaining said prefastened absorbent article in a prefastened condition.

2. The absorbent article of claim 1 wherein said primary fasteners are hook and loop type fasteners.

3. The absorbent article of claim 1 and further comprising at least one attachment panel which is located on said opposite waist region wherein said primary fasteners are configured to releasably engage said attachment panel.

4. The absorbent article of claim 1 and further comprising a pair of secondary fasteners which are located on said one waist region and which are configured to releasably engage said opposite waist region to conform said waist regions to said wearer's body after said prefastened absorbent article is pulled on over a wearer's hips.

5. The absorbent article of claim 1 wherein said primary fasteners are located on said opposed side edges in said back waist region of said absorbent article and releasably engage said front waist region to provide said prefastened absorbent article.

6. The absorbent article of claim 1 wherein said passive side bonds releasably connect said overlapped portion of said one waist region to said side edges of said opposite waist region to assist in maintaining said prefastened absorbent article in said prefastened condition.

7. The absorbent article of claim 6 wherein said passive side bonds releasably connect a waist edge and said side edge of said one waist region to said opposite waist region but do not bond said overlapped portion of said one waist region between said waist edge and said side edge to said opposite waist region.

8. The absorbent article of claim 1 wherein said passive side bonds are located on said one waist region inward from said primary fastener a distance of at least about 1.0 centimeters.

9. The absorbent article of claim 1 wherein said overlapped portion of said one waist region defines an overlap distance of at least about 2.0 centimeters.

10. The absorbent article of claim 1 wherein said passive side bonds include at least one point bond.

11. The absorbent article of claim 10 wherein said point bond is an ultrasonic point bond.

12. The absorbent article of claim 1 wherein said passive side bonds define a peel strength of no more than about 1500 grams.

13. The absorbent article of claim 1 wherein said passive side bonds connect an interior surface of said absorbent article in said one waist region to an outer surface of said absorbent article in said opposite waist region.

14. The absorbent article of claim 1 wherein said passive side bonds connect an interior surface of said absorbent article in said one waist region to an interior surface of said absorbent article in said opposite waist region.

15. A prefastened disposable absorbent article which defines an absorbent, a front waist region, a back waist region, a crotch region which extends between and connects said waist regions and a pair of opposed ear regions on one of said waist regions which overlap said opposite waist region wherein said absorbent article comprises:
   a) a pair of primary fasteners which are located on said opposed ear regions on said one waist region and which are releasably engaged to said opposite waist region of said absorbent article to provide said prefastened absorbent article;
   b) a belt segment which defines opposed end portions and which is located in said one waist region;
   c) a pair of secondary fasteners which are located on said opposed end portions of said belt segment and which are configured to releasably engage said opposite waist region to conform said waist regions to a wearer's body after said prefastened absorbent article is pulled on over a wearer's hips; and
   d) a pair of passive side bonds which are located inward of said primary fasteners on said opposed ear regions in said one waist region and which releasably connect an overlapped portion of said ear regions to said opposite waist region to assist in maintaining said prefastened absorbent article in a prefastened condition.

16. The absorbent article of claim 15 wherein said primary fasteners are located on said ear regions in said back waist region of said absorbent article and releasably engage said front waist region to provide said prefastened absorbent article.

17. The absorbent article of claim 15 wherein said passive side bonds releasably connect said overlapped portion of said ear regions to a pair of opposed side edges of said absorbent article in said opposite waist region.

18. The absorbent article of claim 15 wherein said passive side bonds are not continuous along a longitudinal length of said ear regions.

19. The absorbent article of claim 18 wherein said passive side bonds define an unattached longitudinal length of at least about 1.0 centimeters to create a sleeve through which said belt segment can slidably move.

20. The absorbent article of claim 15 wherein said passive side bonds are located on said ear regions inward from said primary fastener a distance of at least about 1.0 centimeters.

21. The absorbent article of claim 15 wherein said overlapped portion of said ear regions defines an overlap distance of at least about 2.0 centimeters.

22. The absorbent article of claim 15 wherein said passive side bonds include ultrasonic point bonds.

23. The absorbent article of claim 15 wherein said passive side bonds define a peel strength of no more than about 1500 grams.

24. The absorbent article of claim 15 wherein said passive side bonds connect an interior surface of said absorbent article in said one waist region to an outer surface of said absorbent article in said opposite waist region.

25. The absorbent article of claim 15 wherein said passive side bonds connect an interior surface of said absorbent article in said one waist region to an interior surface of said absorbent article in said opposite waist region.

26. The absorbent article of claim 15 and further comprising at least one attachment panel which is located on said opposite waist region and wherein said primary and said secondary fasteners are configured to releasably engage said attachment panel.

27. The absorbent article of claim 15 wherein said absorbent article further includes an outer cover which comprises a nonwoven material.

28. The absorbent article of claim 27 wherein said primary and said secondary fasteners are hook type fasteners which are configured to releasably engage said outer cover.

29. The absorbent article of claim 15 wherein said belt segment comprises an elastic material which is capable of elongating at least about 100 percent.

30. The absorbent article of claim 15 wherein said belt segment is attached to an interior surface of said absorbent article in said one waist region.

31. The absorbent article of claim 30 wherein said opposed end portions of said belt segment extend through slots in said one waist region onto an outer surface of said absorbent article in said one waist region.

32. The absorbent article of claim 15 wherein said secondary fasteners and said opposed end portions of said belt segment are configured to extend over said primary fasteners to releasably engage said opposite waist region of said absorbent article to conform said waist regions to said wearer's body after said prefastened absorbent article is pulled on over a wearers hips.

33. A prefastened disposable absorbent article which defines a front waist region, a back waist region, a crotch region which extends between and connects said waist regions and a pair of opposed side edges, said absorbent article comprising:
   a) an outer cover;
   b) an absorbent chassis which includes a backsheet which is connected to said outer cover, a bodyside liner which is connected to said backsheet in a superposed relation and an absorbent core disposed between said backsheet and said bodyside liner;
   c) a pair of primary fasteners which are located on said outer cover on said laterally opposed side edges of said back waist region of said absorbent article and which are configured to releasably engage an outer surface of said absorbent article in said front waist region of said absorbent article;
   d) a belt segment which is located in said back waist region of said absorbent article and which defines a pair of opposed end portions;
   e) a pair of secondary fasteners which are located on said opposed end portions of said belt segment and which are configured to releasably engage said outer surface of said front waist region to further conform said waist regions to a wearer's body after said prefastened absorbent article is pulled on over a wearers hips; and
   f) a pair of passive side bonds which are located inward of said primary fasteners on said back waist region and which releasably connect an overlapped portion of said back waist region to said front waist region to assist in maintaining said prefastened absorbent article in a prefastened condition.

34. The absorbent article of claim 33 wherein said passive side bonds connect said overlapped portion of said back waist region to said side edges of said front waist region to assist in maintaining said prefastened absorbent article in said prefastened condition.

35. The absorbent article of claim 33 wherein said passive side bonds bond a waist edge and said side edge of said back waist region to said front waist region and but do not bond said overlapped portion of said back waist region between said waist edge and said side edge to said front waist region.

36. The absorbent article of claim 35 wherein said passive side bonds define an unattached longitudinal length of at least about 1.0 centimeters to create a sleeve through which said belt segment can slidably move.

37. The absorbent article of claim 33 wherein said passive side bonds are located on said back waist region inward from said primary fastener a distance of at least about 1.0 centimeters.

38. The absorbent article of claim 33 wherein said overlapped portion of said back waist region defines an overlap distance of at least about 2.0 centimeters.

39. The absorbent article of claim 33 wherein said passive side bonds define a peel strength of no more than about 1500 grams.

40. The absorbent article of claim 33 wherein said passive side bonds connect an interior surface of said absorbent article in said back waist region to an outer surface of said absorbent article in said front waist region.

41. The absorbent article of claim 33 wherein said passive side bonds connect an interior surface of said absorbent article in said back waist region to an interior surface of said absorbent article in said front waist region.

42. A prefastened disposable absorbent article which defines an absorbent, a front waist region, a back waist region, a crotch region which extends between and connects said waist regions and a pair of opposed side edges wherein said absorbent article comprises:

a) a pair of primary fasteners which are located on said opposed side edges in one of said waist regions and which are releasably engaged to said opposite waist region of said disposable absorbent article thereby defining a waist perimeter dimension;

b) a waist size adjustment means for reducing said waist perimeter dimension of said absorbent article without releasing said primary fasteners to conform said waist regions to a wearer's body after said prefastened absorbent article has been pulled on; and c) a pair of passive side bonds which are located inward of said primary fasteners on said one waist region and which releasably connect an overlapped portion of said one waist region to said opposite waist region to assist in maintaining said prefastened absorbent article in a prefastened condition.

43. The absorbent article of claim 42 wherein said waist size adjustment means includes:

a) a belt segment which is located in one of said waist regions wherein said belt segment defines opposed end portions; and b) a pair of secondary fasteners which are located on said opposed end portions of said belt segment and which are configured to releasably engage said opposite waist region to conform said waist regions to said wearer's body.

44. The absorbent article of claim 42 wherein said passive side bonds are located on said one waist region inward from said primary fastener a distance of at least about 1.0 centimeters.

45. The absorbent article of claim 42 wherein said overlapped portion of said one waist region defines an overlap distance of at least about 2.0 centimeters.

46. The absorbent article of claim 42 wherein said passive side bonds define a peel strength of no more than about 1500 grams.

47. The absorbent article of claim 42 wherein said passive side bonds connect an interior surface of said absorbent article in said one waist region to an outer surface of said absorbent article in said opposite waist region.

48. The absorbent article of claim 42 wherein said passive side bonds connect an interior surface of said absorbent article in said one waist region to an interior surface of said absorbent article in said opposite waist region.

* * * * *